United States Patent
Müller

(10) Patent No.: US 6,699,498 B1
(45) Date of Patent: Mar. 2, 2004

(54) TRANSDERMAL THERAPEUTIC SYSTEMS HAVING IMPROVED STABILITY AND THEIR PRODUCTION

(75) Inventor: Walter Müller, Neuwied (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 0 days.

(21) Appl. No.: 09/723,130

(22) Filed: Nov. 27, 2000

(30) Foreign Application Priority Data

Nov. 29, 1999 (DE) .......................... 199 57 401
Nov. 4, 2000 (DE) .......................... 100 54 713

(51) Int. Cl.$^7$ .......................... A61F 13/00; A61K 9/14
(52) U.S. Cl. .................. 424/449; 424/484; 424/485; 424/486; 424/487; 424/488
(58) Field of Search ................ 424/449, 448, 424/443

(56) References Cited

U.S. PATENT DOCUMENTS

| | | | |
|---|---|---|---|
| 4,956,231 A | | 9/1990 | Cavezzan et al. ............ 428/343 |
| 5,527,536 A | * | 6/1996 | Merkle et al. ............... 424/448 |
| 6,113,928 A | * | 9/2000 | Nogueira et al. ............ 424/401 |
| 6,271,256 B1 | * | 8/2001 | Berkowitz et al. .......... 424/653 |

FOREIGN PATENT DOCUMENTS

| | | | |
|---|---|---|---|
| DE | 42 24 325 | | 11/1999 |
| EP | 304 381 | | 2/1989 |
| EP | 441 333 | | 8/1991 |
| EP | 965 626 | | 12/1999 |
| WO | WO 95/29666 | | 11/1995 |
| WO | WO 99/34782 | * | 7/1999 |

OTHER PUBLICATIONS

"Transdermal Controlled Systemic Medications," Yie W. Chien, ed., p. 106, Marcel Dekker, Inc., New York (1987).
Derwent Abstract, 94–163840 published Oct. 1, 1992.

* cited by examiner

*Primary Examiner*—Thurman K. Page
*Assistant Examiner*—Isis Ghali
(74) *Attorney, Agent, or Firm*—Frommer Lawrence & Haug LLP

(57) ABSTRACT

This invention provides for, inter alia, a transdermal therapeutic system comprising at least one therapeutically active substance, which is oxidizable by hydroperoxides, wherein the amount of oxidative degradation of said active substances(s) and the corresponding formation of oxidative degradation products is reduced, which comprises one or more constituents of said transdermal therapeutic system being in contact with said active substance(s), wherein the sum of the peroxide number(s) (PON) of each of said constituents related to their percentage of the whole amount of said constituents as expressed by the formula $$\sum_{i=1}^{n}(N_i \cdot PON/100)$$

where
  N is the percentage content of the whole amount of said constituents in the TTS,
  n is the number of said constituents in the TTS,
  i is the running number
  PON is the peroxide number of each of the constituents, is not greater than 20.

9 Claims, No Drawings

TRANSDERMAL THERAPEUTIC SYSTEMS HAVING IMPROVED STABILITY AND THEIR PRODUCTION

Disregarding a few fairly uncommon special forms, transdermal therapeutic systems (TTS) may be differentiated into two basic groups, those known as matrix systems and those known as reservoir systems. In the case of those known as matrix systems, in the simplest case the active substance is dissolved in a self-adhesive layer or in some cases only suspended in the form of crystals. Reservoir systems represent a type of pouch comprising an inert backing layer and an active substance permeable membrane, the active substance being located in a liquid preparation within this pouch. Usually, the membrane is provided with a layer of adhesive which serves to anchor the system on the skin.

Irrespective of specific embodiments of the transdermal system, the active substance is delivered to the skin by diffusion during use and is therefore required to be present, at least in part, in dissolved form.

In this form, the active substance is particularly sensitive to reactions with constituents of the formulation which may lead to an impairment of the stability. Examples of such reactions include:

a) the bonding of the active substance via an amide or ester bond to carboxyl groups or ester groups of the polymers or permeation enhancers used;

b) the reaction of a carboxyl group or ester group of the active substance with alcoholic groups of tackifying resins or permeation enhancers;

c) the hydrolysis or alcoholysis of ester groups by water or alcohols, respectively.

Such reactions, which may be inferred directly from the functional groups of the active substance and of the auxiliaries, are no surprise to the skilled worker. Corresponding risks to stability are therefore usually discovered very quickly by means of appropriate compatibility studies at elevated temperature and can then be avoided by means of appropriate reformulations of adverse active substance/auxiliary combinations.

Furthermore, the stability of the active substance and of the auxiliaries may be put at risk by reaction with active oxygen. Such active oxygen is, naturally, the oxygen of the air. An effective means of protecting the active substance present in the TTS against this oxygen is to package the TTS under a nitrogen atmosphere and/or to insert antioxidants into the packaging as well.

Despite these precautionary measures, however, it has to date been necessary to accept quite often a greater or lesser decrease in the amount of active substance when a TTS comprising oxidation sensitive active substances is stored for prolonged periods. The causes of this were not previously known.

It has now surprisingly been found that raw materials used to produce TTS may to a considerable extent comprise active oxygen in another form, namely in the form of hydroperoxides.

These hydroperoxides may form by the following mechanism in accordance with the autoxidation reactions described in the literature:

Eq. 1a

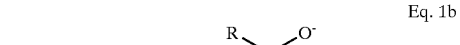

In the first step, known as the induction phase, free radicals are formed by exposure to heat and/or light, promoted by trace amounts of heavy metals and accompanied by the loss of a hydrogen atom. In the second step, known as the propagation phase, these radicals react with oxygen to form peroxy radicals. These peroxy radicals then attack further molecules, forming hydroperoxides and a new free radical. Thus a chain reaction has begun which continues until this chain is terminated by the reaction of two radicals with one another, as shown for example in the equation below.

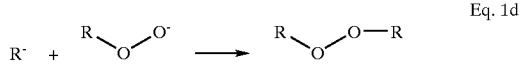

Owing to its relatively low reactivity, the peroxide radical, functioning as a chain transfer agent, attacks particularly those sites which lead to a low-energy radical on the substrate. Preferred sites of this kind are C—H bonds in benzyl or allyl position, tertiary C—H bonds, and C—H bonds in the vicinity of ether oxygens. As a result, raw materials possessing such groups are especially susceptible to the formation of hydroperoxides.

The antioxidants or stabilizers which are used to protect oxidation sensitive active substances may intervene in this reaction chain. Antioxidants may be differentiated into free-radical scavengers and oxygen scavengers. Free-radical scavengers such as tocopherol and its derivatives, for example, remove or inactivate free radicals and so interrupt the chain mechanism of autoxidation. Oxygen scavengers, such as ascorbyl palmitate, for example, react directly with the oxidative agent and so prevent the chain reaction starting.

The addition of antioxidants/stabilizers only makes sense, however, if the starting materials themselves do not comprise hydroperoxides with an oxidative action and if the drug form is protected against the ingress of oxygen by the packaging.

Surprisingly, it has been found that in all classes of raw material used to produce transdermal therapeutic systems, with the exception of materials in film form, there are representatives which on supply or after brief storage are already loaded with considerable amounts of hydroperoxides. Specifically, this means that polymers, tackifying resins, permeation enhancers and solvents or solubilizers may have a hydroperoxide content which can to a considerable extent impair the stability of an oxidation sensitive active substance.

The peroxide content is commonly expressed by means of the so-called peroxide number PON, which indicates the amount of milliequivalents of active oxygen per kg of substance. There are various methods of determining the peroxide number. The most customary is to react a defined amount of substance in a chloroform/glacial acetic acid solution with an excess of iodide ions and then to back-titrate the resultant iodine using sodium thiosulfate. A less common method, which is restricted to aqueous solutions, is to react the substance with titanium(IV) ions and to measure the resultant peroxo complex by photometry. A semiquantitative test for peroxides which is particularly easy to implement is carried out using commercial test electrodes.

The table below lists the measured peroxide numbers of some exemplary substances used to produce reservoir and matrix systems, following approximately 6 months' storage at room temperature. The peroxide numbers were measured by the two first-mentioned methods.

| Raw material | Function | PON |
| --- | --- | --- |
| Hydrocarbon resin | matrix constituent | 180 |
| Collidon | matrix constituent | 110 |
| Partially hydrogenated glycerol ester of rosin | tackifier | 190 |
| Hydrogenated glycerol ester of rosin | tackifier | 80 |
| Poly-β-pinene | tackifier | 150 |
| Diethylene glycol monoethyl ether | solvent/ permeation enhancer | 120 |
| Oleyl alcohol | solvent/ permeation enhancer | 50 |
| Limonene | permeation enhancer | 15 |

The peroxide number of the finished patches may be determined by the same method. However, it is rather difficult to dissolve a sufficient amount of patch in a reasonable amount of chloroform. An easier method is to measure the peroxide loading of the individual substances and to calculate the peroxide number of the active substance component of the patches in accordance with the following formula:

$$\sum_{i=1}^{n} (N_i \cdot PON / 100)$$

n: number of formulation constituents of the active substance component of the system N: percentage content of the formulation constituents in the active substance constituents of the system (numerical value)

PON: peroxide number of the individual constituents of the active substance component of the system It has been found experimentally that the hydroperoxides present in the raw materials may react in diverse ways with the active substance with which they come in contact. Active substances which have been found to be particularly sensitive are those possessing one of the following substructures:

secondary or tertiary amino groups

C—C double bonds

C—H groups in allyl position benzylic C—H groups tertiary C—H groups sulfide or sulfoxide groups The corresponding reaction products are as follows:

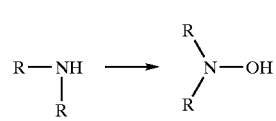

Eq. 2a

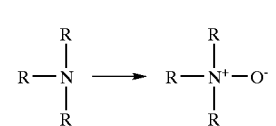

Eq. 2b

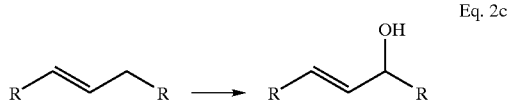

Eq. 2c

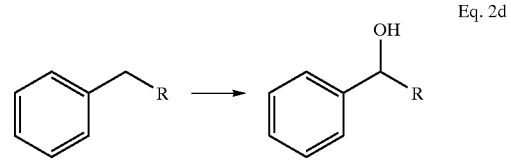

Eq. 2d

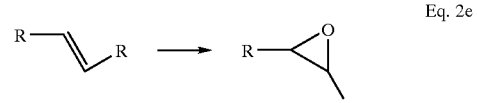

Eq. 2e

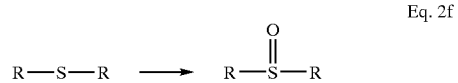

Eq. 2f

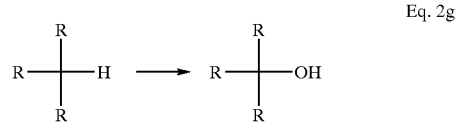

Eq. 2g

R = organic radical

In many cases, these reactions at the corresponding functional groups of the active substances are accompanied by follow-on reactions.

For example, it has been found that, in the case of 17-β-estradiol, initial hydroxylation in the benzyl position (C 9) is followed by elimination of the hydroxyl group in the form of water, accompanied by the formation of Δ9(11) 17-β-estradiol. This reaction is favored since a conjugated double bond is formed as a result.

Eq. 3

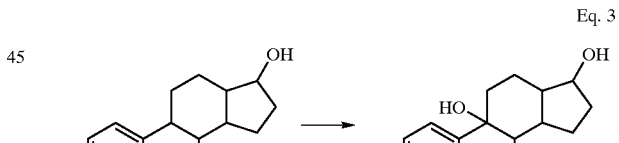

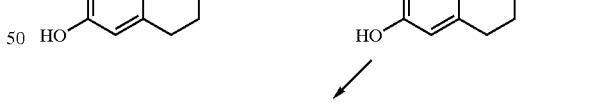

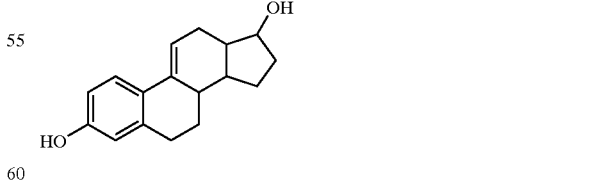

In the case of an active substance having an amine-substituted tetrahydronaphthol fragment (N-0923) it has been found that first of all a N-oxide is formed which then reacts further in an elimination reaction (Cope elimination) in accordance with the reaction scheme below to form a dihydronaphthol and hydroxylamine.

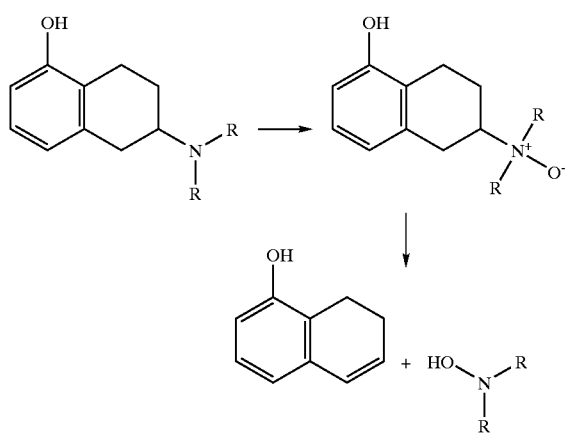

Eq. 4

In the case of calcium antagonists of the dihydropyridine type, the following degradation mechanism was found.

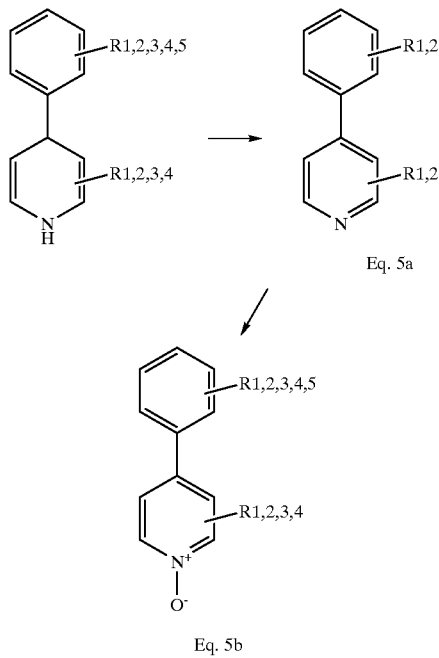

Eq. 5a

Eq. 5b

It is unclear whether the first attack takes place on the nitrogen or on the tertiary C—H bond of the dihydropyridine ring. In any case, what follows here again is elimination of water, which is energetically favored owing to the formation of an aromatic state. The subsequent reaction to the N-oxide following oxidation of the dihydropyridine ring is observed only in the reaction with t-butyl hydroperoxide in accordance with equation 5b. In patch systems, the amount formed is too small to be observed at low conversions.

The examples depicted above show that from the reaction products it is often not possible to perceive that hydroperoxides have participated directly in the degradation reaction. To determine the sensitivity of the active substance to oxidation reactions with hydroperoxides, an easily implemented test reaction has been developed. For this purpose, the active substance in chloroform or another appropriate solvent is reacted with t-butyl hydroperoxide under reflux. If oxidative degradation products of the active substance are found in this reaction mixture, they can be attributed to the reaction with hydroperoxide. Often, degradation of the active substance is also evident very simply from a discoloration of the test solution. The practical conclusion to be drawn from a positive outcome of the test reaction is that when formulating a transdermal system using this active substance the auxiliaries used should include only those which are substantially free from hydroperoxides.

The object on which the present invention is based is to provide a transdermal therapeutic system (TTS) in which the formation of oxidative degradation products of the oxidation sensitive active substances present in said TTS is reduced during the storage of said TTS. As already set out above, this object is achieved by using only those formulation constituents which are substantially free of hydroperoxides when producing a TTS comprising one or more oxidation sensitive active substances. In accordance with the invention, these formulation constituents are those which, together, in the proportions provided by the recipe for the TTS, have a peroxide number (PON) of not more than 20, preferably not more than 10, with particular preference not more than 5.

The term formulation constituents embraces all substances of the TTS—with the exception of the pharmaceutical active substance or substances—in which the active substance(s) are present.

They include: as building blocks of the single-layer or multilayer matrix or of the reservoir system: e.g., polymers of hydrocarbons such as polyethylenes, polypropylenes, polyacrylates, polymethacrylates, polyurethanes, polyisobutylenes, polyvinylpyrrolidone; hydrocarbon resins; silicones; rubber; copolymers of vinylpyrrolidone with acrylic acids, acrylic acid derivatives, ethylene and/or vinyl acetate; resins based on rosin derivatives and/or polyterpenes. As functional additives or auxiliaries: e.g., plasticizers and tackifiers such as rosin esters, examples being hydrogenated or partially hydrogenated glycerol esters of rosin, polyterpenes; permeation enhancers such as terpenes or terpene derivatives, unsaturated fatty acids or their derivatives, esters of long-chain fatty acids, diethylene glycol or its derivatives, for example; alkylmethyl sulfoxides, azones and limonenes; crystallization inhibitors such as polyvinylpyrrolidone, for example; polyacrylic acid or cellulose derivatives; solvents such as polyethylene glycol, diethylene glycol and/or its derivatives, propanediol or oleyl alcohol, for example.

If formulation constituents intended for the production of transdermal therapeutic systems comprising oxidation sensitive active substances are already loaded with considerable amounts of hydroperoxides when supplied, these substances need to be substantially freed from hydroperoxides prior to use. This can be done by destroying hydroperoxides by means of strongly reducing substances. A highly suitable reducing agent and pharmaceutically permitted auxiliary is, for example, sodium bisulfite or sodium hydrogen sulfite. In aqueous or predominantly aqueous solution, this substance can be used to destroy peroxides without problems in a quick reaction. Unfortunately, however, the majority of auxiliaries and polymers used for transdermal systems either are insoluble in water or else water is not compatible with the other auxiliaries used. Surprisingly, it has now also been found that the destruction of hydroperoxides is also possible if the solid substance is dissolved in a water-miscible solvent, preferably ethanol or methanol, and an aqueous solution of an inorganic sulfite, e.g., sodium hydrogen sulfite, is slowly added with stirring to the first solution. Although instances of precipitation occur very quickly when the sulfite solution is added to the solution of the auxiliary, the sulfites still have sufficient time to destroy the hydroperoxides by reduction.

If the solution of the hydrogen sulfite has a sufficient concentration, the small amount of water introduced can usually be tolerated without problems. This is especially the case when the water is removed together with other solvents during coating and drying. Liquid auxiliaries may be reacted with an aqueous solution of sodium hydrogen sulfite even without additional solvent.

Following this treatment, the materials are virtually free from peroxides and may be used without concern even if loaded considerably beforehand. An additional improvement in stability may be achieved by the addition of antioxidants, which retard or suppress the formation of new peroxides during the storage of the systems.

Regarding the tolerable upper limit of the peroxide content of the constituents in contact with the active substance, an upper peroxide number limit of 20, better still 10, preferably 5, should not be exceeded.

The limit of 10 is a result of the following exemplary calculation on a typical transdermal therapeutic matrix system having a size of 20 cm$^2$ and a coating weight of 100 g/m$^2$ and an active substance concentration of 10% g/g. For an assumed molecular weight of the active substance of 200 daltons, accordingly, the system contains 20 mg or 0.1 mmol of active substance, and, with a peroxide number of 10, a total of $0.2 \cdot 10^{-2}$ mmol of active oxygen. This means that not more than 2% of the active substance present in the system may be oxidized. In view of the fact that this reaction needs time and is retarded by the consumption of active oxygen, there is a good chance—with a peroxide number of 10, and under certain circumstances an upper limit of 20—that the system will be sufficiently stable for 2 years.

Improved stability is of course achieved by reducing the peroxide loading further (preferably to a PON of 5 or less); by treating the peroxide-loaded auxiliaries with sulfites in accordance with the method described and/or choosing auxiliaries which do not tend to form peroxides.

EXAMPLE

Example 1

80 ml of chloroform and 1 g of t-butyl hydroperoxide are added to 0.5 g of the active substance and this system is heated under reflux with stirring for 6 hours. The reaction mixture is subsequently assessed for its color and analyzed using an appropriate chromatographic method for degradation products formed.

Example 2

Stability of N-0923 base in matrices with peroxide number 38 and peroxide number 2.6

Degradation in accordance with equation 4, indentified oxidative degradation product: 1,2-dihydronaphth-8-ol

| Matrix 2a: peroxide number 38 | |
|---|---|
| Styrene/polyisobutylene/styrene block polymer | 16% |
| Oleyl alcohol | 10% |
| Hydrocarbon resin | 22% |
| Glycerol ester of partially hydrogenated rosin | 22% |
| Polyisobutylene | 7% |
| Paraffin, liquid | 3% |
| N-0923 base | 20% |

| Matrix 2b: peroxide number 2.6 | |
|---|---|
| Polyacrylate adhesive | 60% |
| Oleyl alcohol | 10% |
| N-0923 base | 30% |

Active substance content after 3 months, based on the initial content of 100%

| | Matrix 2a | Matrix 2b |
|---|---|---|
| 25° C. | 85% | 99.5% |
| 40° C. | 44% | 89.9% |

Oxidative degradation product 1,2-dihydronaphth-8-ol in area percent of the HPLC chromatograms

| | Matrix 2a | Matrix 2b |
|---|---|---|
| 25° C. | 8.1% | unquantifiable |
| 40° C. | 34.1% | 0.4% |

Identified degradation product, found in reaction with t-butyl hydroperoxide in accordance with example 1: 1,2-dihydronaphth-8-ol

Example 3

Stability of estradiol in matrices with peroxide number 35 and peroxide number 2

| Matrix 3a: peroxide number 35 | |
|---|---|
| Polyacrylate adhesive | 16% |
| Glycerol | 10% |
| Glycerol ester of partially hydrogentated rosin | 22% |
| Estradiol | 20% | corresponds to matrix 3a but using glycerol ester of partially hydrogenated rosin, treated with Na bisulfite solution Δ9(11) 17β-Estradiol content in matrices after 6 months, Area percentages in HPLC chromatograms

| | Matrix 3a | Matrix 3b |
|---|---|---|
| 25° C. | 0.43% | undetectable |
| 40° C. | 0.75% | undetectable |

Example 4

Stability of bopindolol in peroxide-rich and low-peroxide matrix

| Matrix composition | |
|---|---|
| Bopindolol: | 15% |
| Polyacrylate adhesive: | 65% |
| Glycerol ester of partially hydrogenated rosin: | 20% |

Matrix 4a:
prepared with glycerol ester of partially hydrogenated rosin having a PON of 160

Matrix 4b:
prepared with glycerol ester of partially hydrogenated rosin treated with Na bisulfite solution

|  | Matrix 4a | Matrix 4b |
|---|---|---|
| 30 days at 40° C. | brown discoloration | no discoloration |

The reaction with t-butyl hydroperoxide in accordance with example 1 very rapidly produces a yellowish discoloration which then becomes strongly brown.

It was not possible to clarify the structure of the degradation products.

Example 5

Stability of nifedipine in peroxide-rich and low-peroxide reservoir

Degradation products after oxidation with t-butyl hydroperoxide

I.) Aromatization of the dihydropyridine ring in accordance with equation 5a

II) N-oxide formation in accordance with equation 5b

| Nifedipine: | 10% |
|---|---|
| Diethylene glycol monoethyl ether | 90% |

Reservoir 5b:
prepared with diethylene glycol monoethyl ether treated with sodium bisulfite solution

| 30 days | Reservoir 5a Degradation prod. I | Reservoir 5b Degradation prod. I |
|---|---|---|
| 25° C. | 1.6% | unquantifiable |
| 40° C. | 4.5% | 0.3% |

Degradation product II, in accordance with equation 5b, was not found owing to the low concentration in the systems.

Example 6

Stability of pergolide in peroxide-rich and low-peroxide matrix

Identified degradation product after oxidation with t-butyl hydroperoxide:

Oxidation of the sulfide sulfur to the sulfoxide

Matrix 6a, PON: about 32

| Pergolide: | 10% |
|---|---|
| Polyacrylate adhesive: | 70% |
| Glycerol ester of partially hydrogenated rosin: | 20% |

Matrix 6b, PON: about 2–3

| Pergolide: | 10% |
|---|---|
| Polyacrylate adhesive: | 90% |

| 30 days | Matrix 6a Sulfoxide | Matrix 6b Sulfoxide |
|---|---|---|
| 25° C. | 0.8% | unquantifiable |
| 40° C. | 4.2% | unquantifiable |

Example 7

Destruction of Peroxides Using Sodium Bisulfite Solution

The raw material to be treated is dissolved in a water-miscible solvent, preferably methanol or ethanol, and this solution is admixed with stirring with an approximately 10–30 percent strength solution of sodium bisulfite (sodium hydrogen sulfite). The amount of sodium bisulfite solution is such that, by stoichiometry, all of the peroxides, or all of the peroxides to a sufficient degree, are destroyed.

The precipitating reaction product of sodium hydrogen sulfite, sodium hydrogen sulfate, can be separated off, if desired or necessary, by centrifugation or sedimentation or filtration.

What is claimed is:

1. A transdermal therapeutic system ("TTS") comprising, as constituents, a) at least one therapeutically active substance, which contains at least one secondary or tertiary amino group, one double bond, one C—H bond in allyl position, one C—H bond in benzyl position, one tertiary C—H bond or one sulfide group which are oxidizable by hydroperoxides; and b) a single-layer or multilayer matrix system, wherein the matrix system contains the active substance and comprises at least one member selected from the group consisting of hydrocarbon resins, polyvinylpyrrolidone and copolymers of vinylpyrrolidone with acrylic acids, acrylic acid derivatives, ethylene or vinyl acetate, whereby, the sum of the peroxide number(s) (PON) of each of said constituents related to their percentage of the whole amount of said constituents, as expressed by the formula $$\sum_{i=1}^{n} (N_i \cdot PON/100)$$

where
N is the percentage content of the whole amount of said constituents in the TTS,
n is the number of said constituents in the TTS,
i is the running number
PON is the peroxide number of each of the constituent(s),
is not greater than 20 which is obtained by a process comprises:

a) if the sum of the peroxide number of the formulation constituents is greater than 20, treating the constituents with a reducing substance and continue with step c);

b) if the sum of the peroxide number(s) is less than or equal to 20, continuing with step c);

c) preparing the transdermal therapeutic system by combining the therapeutic substance(s) with the formulation constituent(s).

2. The transdermal therapeutic system according to claim 1, wherein said sum of peroxide numbers is not greater than 10.

3. The transdermal therapeutic system according to claim 1, wherein said sum of peroxide numbers is not greater than 5.

4. The transdermal therapeutic system according to claim 1, wherein at least one of the constituents comprises one or more self-adhesive containing layers, which comprise the active substance(s) and tackifying resins based on rosin derivatives and/or polyterpenes.

5. The transdermal therapeutic system according to claim 1, wherein said constituents comprise permeation enhancers and/or crystallization inhibitors.

6. The transdermal therapeutic system according to claim 1, which is a reservoir system and wherein the oxidizable active substance is dissolved in a solvent or solvent mixture possessing at least one ether oxygen, tertiary carbon atom or C—H group in allyl position.

7. The transdermal therapeutic system according to claim 5, wherein the permeation enhancer(s) is selected from the group consisting of terpenes, terpene derivatives, unsaturated fatty acids and their derivatives, fatty alcohols and their derivatives, and diethylene glycol and its derivatives.

8. The transdermic therapeutic system according to claim 1, wherein the reducing substance is a sodium sulfite or sodium hydrogen sulfite in an aqueous lower-alkanoic solution.

9. The transdermic therapeutic system according to claim 5, wherein the aqueous lower-alkanoic solution is a methanolic or an ethanolic solution.

* * * * *